United States Patent [19]

Fabian et al.

[11] Patent Number: 5,431,625

[45] Date of Patent: Jul. 11, 1995

[54] IONTOPHORESIS ELECTRONIC DEVICE HAVING A RAMPED OUTPUT CURRENT

[75] Inventors: Liboslav Fabian, New Brighton; Thomas J. Williams, Oak Grove, both of Minn.

[73] Assignee: Empi, Inc., St. Paul, Minn.

[21] Appl. No.: 984,303

[22] Filed: Dec. 1, 1992

Related U.S. Application Data

[63] Continuation-in-part of Ser. No. 649,495, Feb. 1, 1991, Pat. No. 5,254,081.

[51] Int. Cl.⁶ ............................................. A61N 1/30
[52] U.S. Cl. .................................... 604/20; 607/63; 607/72
[58] Field of Search ............... 604/20, 290; 607/63, 607/153, 64, 72, 74, 75

[56] References Cited

U.S. PATENT DOCUMENTS

| | | |
|---|---|---|
| 3,618,601 | 11/1971 | Richardson . |
| 3,991,755 | 11/1976 | Vernon et al. . |
| 4,088,141 | 5/1978 | Niemi ........................ 607/63 |
| 4,141,359 | 2/1979 | Jacobsen et al. . |
| 4,149,533 | 4/1979 | Ishikawa et al. . |
| 4,166,475 | 9/1979 | Gano . |
| 4,185,640 | 1/1980 | Kastrubin et al. ............ 607/63 X |
| 4,250,878 | 2/1981 | Jacobsen et al. . |
| 4,301,794 | 11/1981 | Tapper . |
| 4,340,047 | 7/1982 | Tapper et al. . |
| 4,406,658 | 9/1983 | Lattin et al. . |
| 4,416,274 | 11/1983 | Jacobsen et al. . |
| 4,419,092 | 12/1983 | Jacobsen et al. . |
| 4,457,748 | 7/1984 | Lattin et al. . |
| 4,564,016 | 1/1986 | Maurice et al. . |
| 4,585,652 | 4/1986 | Miller et al. . |
| 4,702,732 | 10/1987 | Powers et al. . |
| 4,738,250 | 4/1988 | Fulkerson et al. ............ 607/63 X |
| 4,786,277 | 11/1988 | Powers et al. . |
| 4,850,956 | 7/1989 | Bontemps . |
| 4,931,046 | 6/1990 | Newman . |
| 4,979,938 | 12/1990 | Stephen et al. . |
| 5,019,034 | 5/1991 | Weaver et al. . |
| 5,037,380 | 8/1991 | Jacobsen et al. . |
| 5,042,975 | 8/1991 | Chien et al. ............ 604/20 |
| 5,047,007 | 9/1991 | McNichols et al. . |
| 5,087,242 | 2/1992 | Petelenz et al. . |
| 5,125,894 | 6/1992 | Phipps et al. . |

OTHER PUBLICATIONS

Sorenson et al., Registration No. H71, Published Jun. 3, 1986.
Lattin et al., Registration No. H516, Published Sep. 6, 1988.
Life-Tech, Inc. product literature for: Iontophor-PM ™ model 6110PM.
Packed Power, *Principles of Power Conversion.*

*Primary Examiner*—Lee S. Cohen
*Assistant Examiner*—Jeffrey R. Jastrzab
*Attorney, Agent, or Firm*—Kinney & Lange

[57] ABSTRACT

An iontophoresis controller is configured for connection to an iontophoresis electrode pair. The controller controls infusion of a selected dose of ionic drugs into a patient through the electrode pair during a treatment period. The controller includes an electrode driver channel having an electrode output configured for electrical connection to the electrode pair. The electrode driver channel delivers a substantially constant electrode output current at a selected treatment level through the electrode output during the treatment period. The electrode output current rises exponentially from approximately zero to the selected treatment level, remains at the selected treatment level during the treatment period, and then falls exponentially to approximately zero. A microprocessor controls operation of the electrode driver channel to generate the electrode output current during the treatment period.

12 Claims, 6 Drawing Sheets

IONTOPHORESIS ELECTRONIC DEVICE HAVING A RAMPED OUTPUT CURRENT

CROSS REFERENCE TO RELATED APPLICATION

This application is a continuation-in-part of U.S. application Ser. No. 07/649,495, filed Feb. 1, 1991, now U.S. Pat. No. 5,254,081.

BACKGROUND OF THE INVENTION

The present invention relates to an iontophoresis medication delivery system for controlling infusion of ionic drugs in medical iontophoresis. In particular, the present invention relates to an iotophoresis medication delivery system having an exponentially ramped output current.

Iontophoresis medication delivery systems transfer ionized molecules of a drug solution through a patient's skin. Drug migration is achieved by placing two electrodes on the patient's skin which are connected to an electric direct-current (DC) power supply. One of the electrodes is a source or "active" electrode filled with a drug solution. The other electrode is a return or "inactive" electrode filled with an electrolyte solution. The current delivered to the electrodes generates an electric field between the two electrodes which causes the ionized drug molecules to migrate from the active electrode into the tissues and bloodstream of the patient without the necessity of a hypodermic injection and its adverse effects.

However, patients may experience a shocking or stunning sensation during rapid changes in current level when the delivered current is turned on or turned off. This sensation can be minimized by ramping the current up from zero when the device is turned on and ramping the current down to zero when the device is turned off.

A linear ramp increases and decreases the delivered current slowly over time. An incremental ramp increases and decreases the delivered current in fixed increments over time. While the linear ramp and the incremental ramp reduce some of the discomfort experienced by the patient, the ramps are relatively inefficient since they significantly add to the total treatment time for delivery of a selected drug dose. For example, the linear ramp may take up to one minute to ramp the output current up from zero milliamperes to four milliamperes. If the rate of change of current is increased significantly, the ramp may not have an appreciable effect on patient comfort.

Lattin et al. U.S. Pat. No. 4,406,658 and 4,457,748 disclose an iontophoretic device having a current control circuit which is applied to a pair of electrodes. The current control circuit includes an output transistor having a base connected to a capacitor. A pair of constant current diodes cause the charge on the capacitor and on the base of the output transistor to charge linearly. As the base of the transistor charges, the output current ramps up gradually from zero to a full current value over a period of about one second.

Jacobsen et al. U.S. Pat. No. 4,141,359 discloses an epidermal iontophoresis device which includes a damping circuit to preclude sudden changes in current experienced when the device is turned on or turned off. The damping circuit limits incremental increases of current to minimize discomfort. Newman U.S. Pat. No. 4,931,046 discloses an iontophoresis drug delivery system in which the amplitude level of current pulses is increased in discrete steps (0.1 milliamperes) from a relatively low level to a selected operating level.

SUMMARY OF THE INVENTION

The present invention is an electric, iontophoresis device which maximizes patient comfort while minimizing drug delivery time. The device is configured for connection to at least one iontophoresis electrode pair for controlling infusion of a selected dose of ionic drugs into the patient through the electrode pair. The device includes an electrode driver channel for connection to the electrode pair. The electrode driver channel includes an electrode output configured for delivering a substantially constant output current to the electrode pair. The output current rises exponentially from approximately zero to a selected treatment current intensity, remains at the selected treatment current intensity during a treatment period, and then falls exponentially to approximately zero. A microprocessor operates the electrode driver channel to generate the output current during the treatment period.

Patients can tolerate larger changes in current at low current levels than at high current levels. The exponential current ramp provides a relatively high rate of change of current at low current levels and a relatively low rate of change of current at high current levels to maximize patient comfort while minimizing drug delivery time. For example, the exponential current ramp may take only 30 seconds to ramp an output current up from zero milliamperes to four milliamperes.

In one embodiment, the microprocessor includes a ramp output for selectively generating a ramp voltage. The electrode driver channel includes an RC circuit which is connected to the ramp output and has a resistance and a capacitance for generating a RC output voltage in response to the ramp voltage. The RC output voltage rises exponentially from approximately zero to the ramp voltage when the microprocessor generates the ramp voltage on the ramp output. The RC output voltage falls exponentially from the ramp voltage to approximately zero when the microprocessor removes the ramp voltage from the ramp output.

An amplifier is connected to the RC circuit in a voltage follower configuration for receiving the RC output voltage and for generating an amplifier output which follows, and is isolated from, the RC output voltage. An adjustable voltage divider is connected to the amplifier output for generating a treatment control voltage which has a magnitude that is a function of the RC output voltage and an adjustment of the adjustable voltage divider. The magnitude of the treatment control voltage determines the output current intensity delivered through the electrode output. The patient or treating physician can adjust the output current intensity by adjusting the adjustable voltage divider.

The electrode driver channel further includes a pulse width modulator and a transformer connected as a "flyback" regulator for controlling the level of current delivered through the electrode output. The pulse width modulator has a modulation control input, a modulation feedback input and a pulse width modulated output. The modulation control input is connected to the adjustable voltage divider for receiving the treatment control voltage. The modulated output generates a pulse width modulated signal having a pulse width which is a function of the treatment control voltage and a modulation feedback voltage applied to the modulation feedback input.

The transformer generates the electrode output current through the electrode output in response to the pulse width modulated signal. A rectifier is connected to the transformer for rectifying the electrode output current.

A modulation feedback circuit is connected between the electrode output and the modulation feedback input. The modulation feedback circuit generates the modulation feedback voltage as a function of the electrode output current such that the modulation feedback voltage follows the treatment control voltage.

As the treatment control voltage rises exponentially to the treatment level, it becomes greater than the modulation feedback voltage. The pulse width modulator increases the pulse width exponentially with the increasing treatment control voltage. The transformer increases the electrode output current exponentially in response to the increasing pulse width. Finally, the modulation feedback voltage rises exponentially in response to the rising electrode output current and thereby follows the treatment control voltage.

As the treatment control voltage reaches the treatment level, the pulse width modulator regulates the pulse width to maintain a constant electrode output current. The microprocessor monitors the delivered output current and calculates the total dose (in milliampere-minutes) delivered to the patient through the electrode output. When the delivered dose reaches the dose prescribed by the physician, the microprocessor removes the ramp voltage from the ramp output. The RC output voltage and the treatment control voltage decay exponentially causing the pulse width of the modulated output signal to decrease exponentially, which causes the electrode output current to decrease exponentially. The exponential rise and fall of the output current minimizes drug delivery time while maximizing patient comfort.

BRIEF DESCRIPTION OF THE DRAWINGS

FIG. 3e is a block diagram which illustrates how FIG. 3a, 3b, 3c and 3d are to be arranged.

DETAILED DESCRIPTION OF THE PREFERRED EMBODIMENTS

The present invention is an iontophoresis electronic device having a ramped output current. The output current rises exponentially from zero to a treatment level, remains at the treatment level for a treatment period, and then falls exponentially from the treatment level to zero. The exponential rise and fall of the output current maximizes patient comfort while minimizing drug delivery time.

Figure 1:
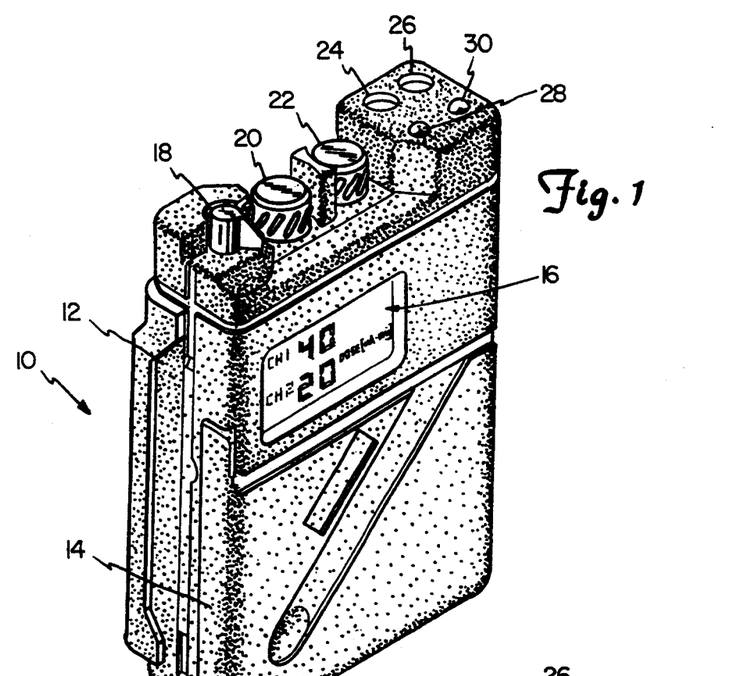
FIG. 1 is a perspective view of a multiple site drug iontophoresis electronic device, in accordance with the present invention.

FIG. 1 is a perspective view of a multiple site drug iontophoresis electronic device 10 in accordance with the present invention. Iontophoresis device 10 is capable of driving a plurality of electrodes with a single controller. The electrodes are driven by a plurality of electrically isolated electrode driver channels which have independently controlled current intensity. Each electrode driver channel includes an exponential output current ramp in accordance with the present invention. The iontophoresis device shown in FIG. 1 includes two driver channels which deliver twice the total quantity of drugs at one-half the electrical current level, as compared to a single driver channel.

Iontophoresis device 10 includes housing 12, flip-cover 14, liquid crystal display (LCD) 16, treatment control switch 18, channel 1 current intensity knob 20, channel 2 current intensity knob 22, electrode output jacks 24 and 26 and light emitting diodes (LEDs) 28 and 30.

Iontophoresis device 10 is connected to a patient through one or two pair of electrodes (not shown). One of the electrodes in each pair is a source or "active" electrode filled with a drug solution. The other electrode in each pair is a return or "inactive" electrode filled with an electrolyte solution. Each pair of electrodes is connected to iontophoresis device 10 through lead wires coupled to a plug which is inserted into either electrode output jack 24 or 26. Jacks 24 and 26 each include tip and sleeve contacts for connection to the plug.

Channel 1 current control knob 20 and channel 2 current control knob 22 determine the intensity of current delivered through electrode output jacks 24 and 26, respectively. Current flow through electrode output jacks 24 and 26 generate an electric field between the active and inactive electrodes which causes the ionized drug molecules to migrate from the active electrodes into the tissue and bloodstream of the patient.

LCD display 16 displays useful parameters to the patient. In the embodiment shown in FIG. 1, LCD display 16 displays time remaining (minutes), dosage delivered (milliampere-minutes), and current level (milliamperes) for each channel. These parameters may be selected from switches located beneath flip-cover 14. For example, in FIG. 1, LCD display 16 displays a dose of 40 milliampere-minutes delivered through channel 1 and a dose of 20 milliampere-minutes delivered through channel 2.

Figure 2:
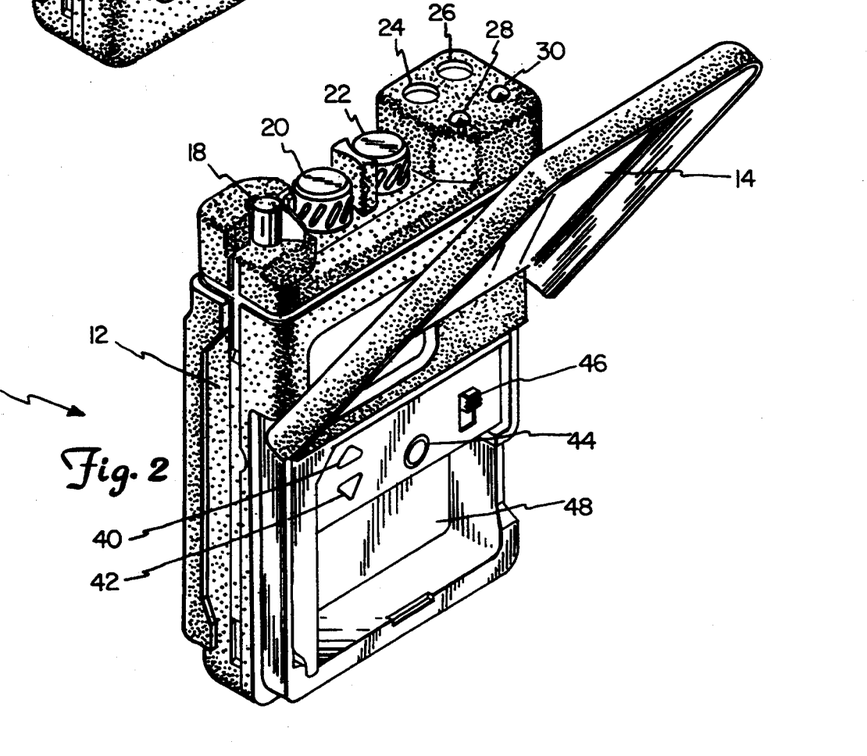
FIG. 2 is a perspective view of the device of FIG. 1 with a flip-cover raised to expose additional treatment and display controls.

FIG. 2 is a perspective view of iontophoresis device 10 with flip-cover 14 raised to expose dose increment switch 40, dose decrement switch 42, display selector switch 44, power switch 46, and battery compartment 48. Display selector switch 44 determines whether time, dose or current is displayed on LCD display 16. In one embodiment, switches 40, 42 and 44 are momentary contact push button switches. A 9-volt battery (not shown) supplies power to the electrical components that form iontophoresis device 10. The 9-volt battery is positioned within battery compartment 48.

Treatment control switch 18 (shown in FIG. 1) selects from four operational modes including setup channel 1 (S1), setup channel 2 (S2), pause (P), and run (R). Setup modes S1 and S2 allow each channel to be programmed independently. In setup mode, the patient selects the dose display on LCD display 16 using display selector switch 44 and enters a prescribed dose in milliampere-minutes by depressing dose increment switch 40 to increase the dose and dose decrement switch 44 to decrease the dose.

In pause mode, iontophoresis device 10 "powers-up" each electrode driver channel while disabling the electrode outputs. The patient can adjust the selected current intensity for each channel while monitoring the current intensity on LCD display 16, without delivering any current through electrode output jacks 24 and 26.

When the patient moves treatment control switch 18 from pause to run mode, iontophoresis device 10 enables the electrode outputs and operates each electrode driver channel to ramp the output current up exponentially from zero to the selected current intensity. Iontophoresis device 10 delivers the output current at the selected current intensity for a treatment period. The treatment period is determined by the dose parameter supplied by the patient and the selected current intensity.

The selected current intensity can be adjusted in either pause mode or run mode. Iontophoresis device 10 automatically recalculates the time remaining to deliver the prescribed dose based on the adjustment in current intensity. At the end of the treatment period, the output current ramps down exponentially from the selected current intensity to zero.

The exponential rise and fall of the output current minimizes the shocking or stunning sensations experienced by the patient when the delivered current is turned on or turned off. In one embodiment, the output current ramps up and ramps down in approximately 30 seconds. Iontophoresis device 10 bypasses the output current ramp during pause mode to allow the patient or physician to rapidly select the current intensity for each channel without having to wait for the output current to ramp up or ramp down.

Iontophoresis device 10 includes annunciators which supply the patient with warning signals when the output current intensity in channel 1 or channel 2 drops below a specified level, or when various other fault conditions occur. The annunciators provide both visual and audible alerts to the patient. LEDs 28 and 30 provide the visual alert to the patient while a buzzer (not shown) provides the audible alert. LED 28 alerts the patient to fault conditions occurring in channel 1 and in the electrode pair connected to jack 24. LED 30 alerts the patient to fault conditions occurring in channel 2 and in the electrode pair connected to jack 26. During normal operation, LEDs 28 and 30 illuminate when current is being delivered through output jacks 24 and 26, respectively.

Figure 3A:
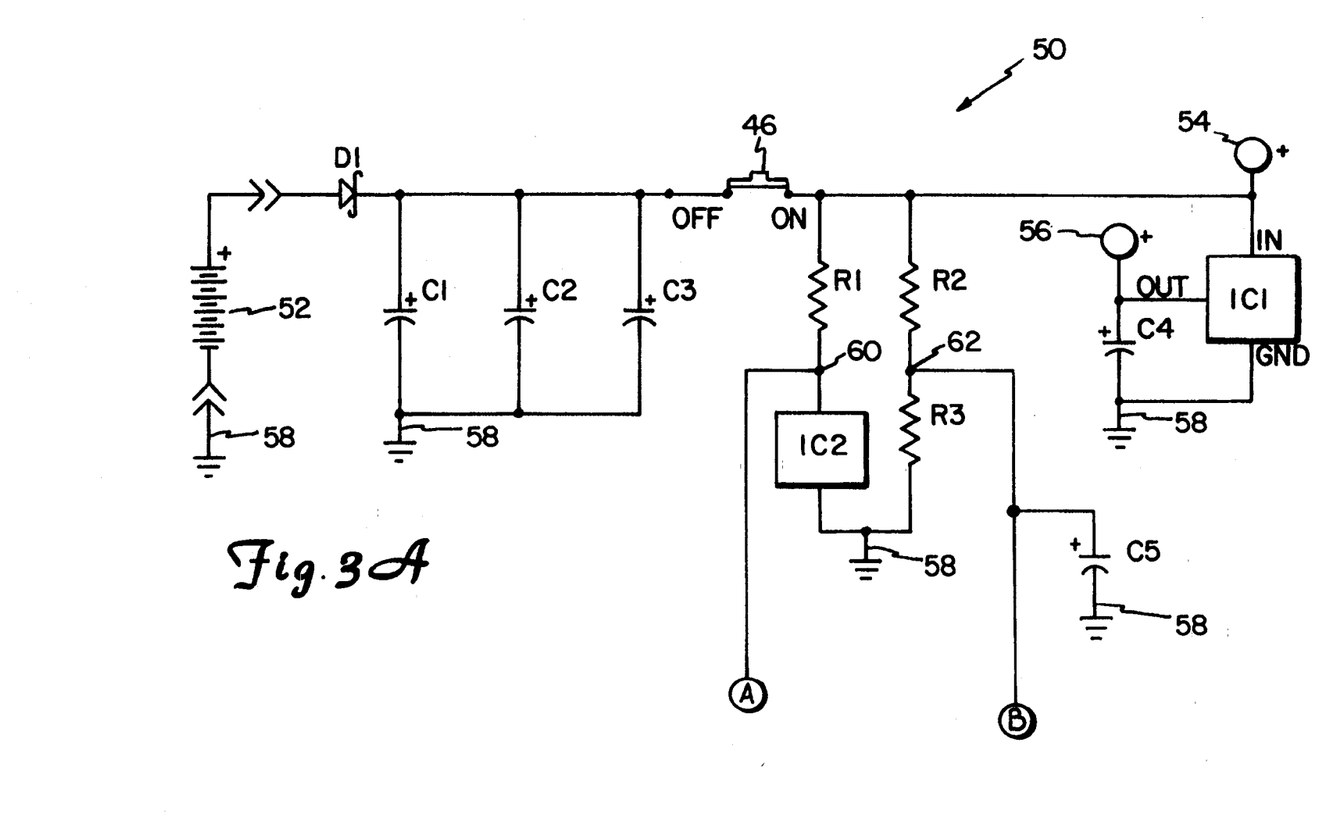
FIGS. 3a, 3b, 3c and 3d together form a detailed schematic diagram of the device shown in FIGS. 1 and 2.
Figure 3B:
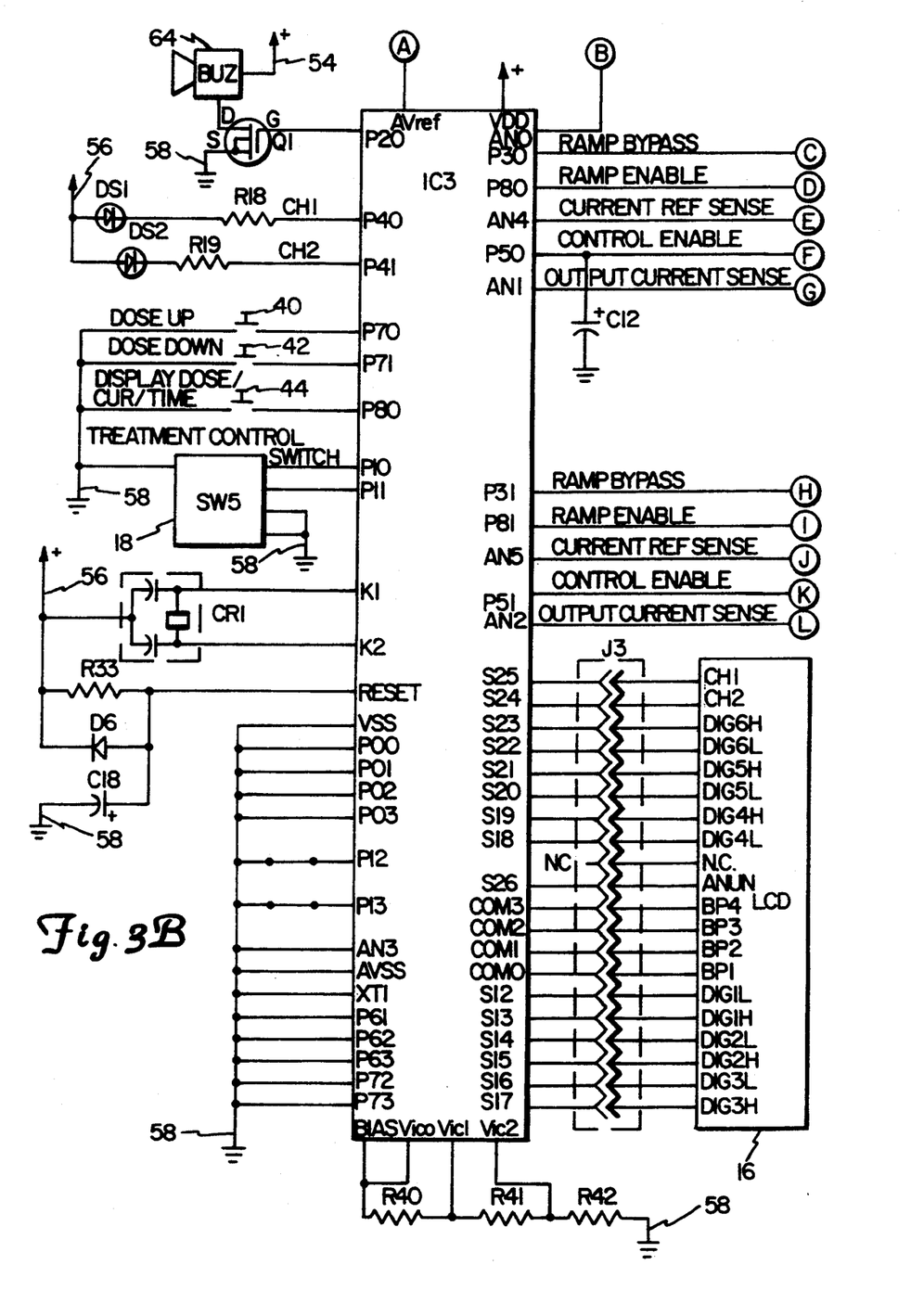
Figure 3C:
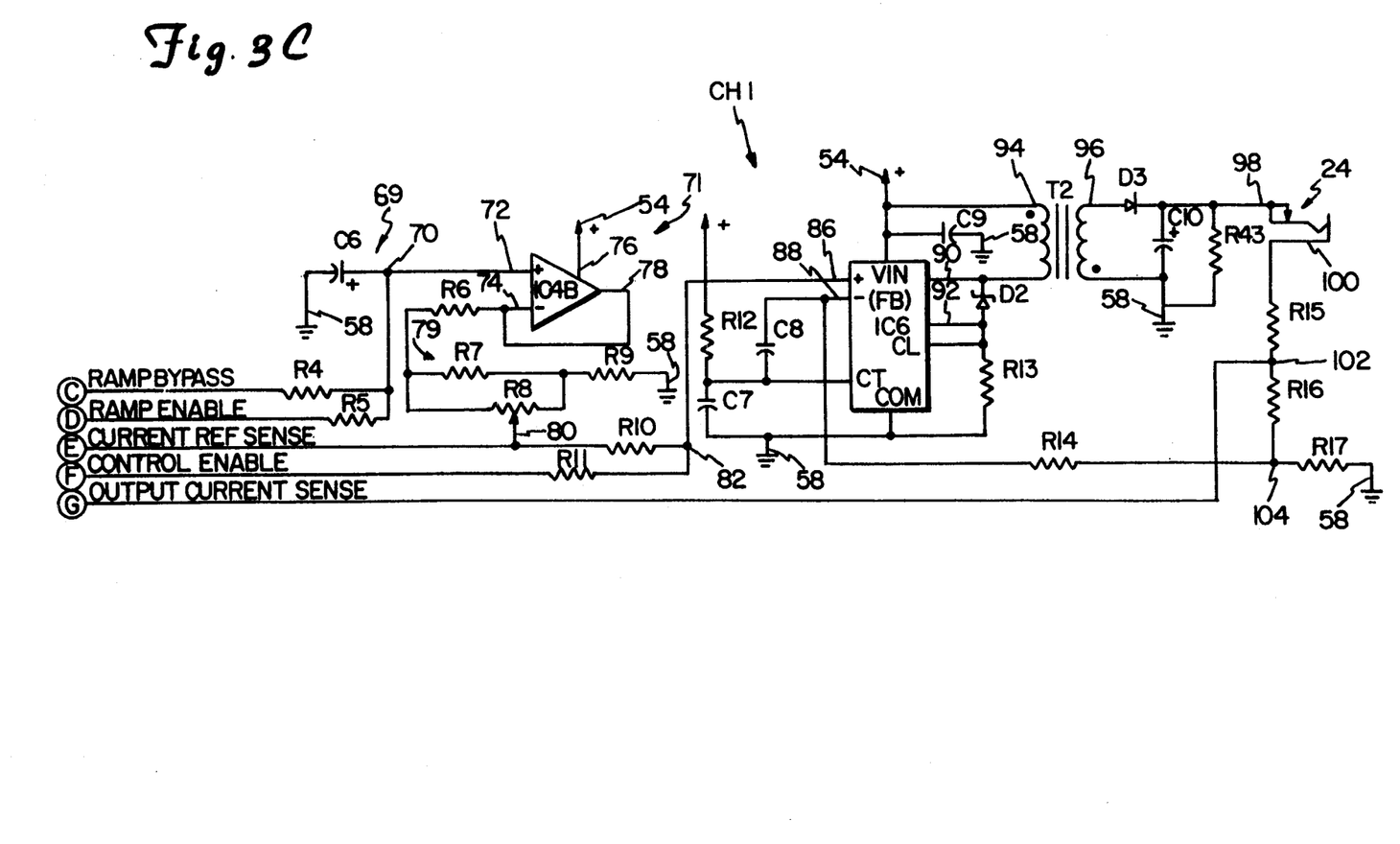
Figure 3D:
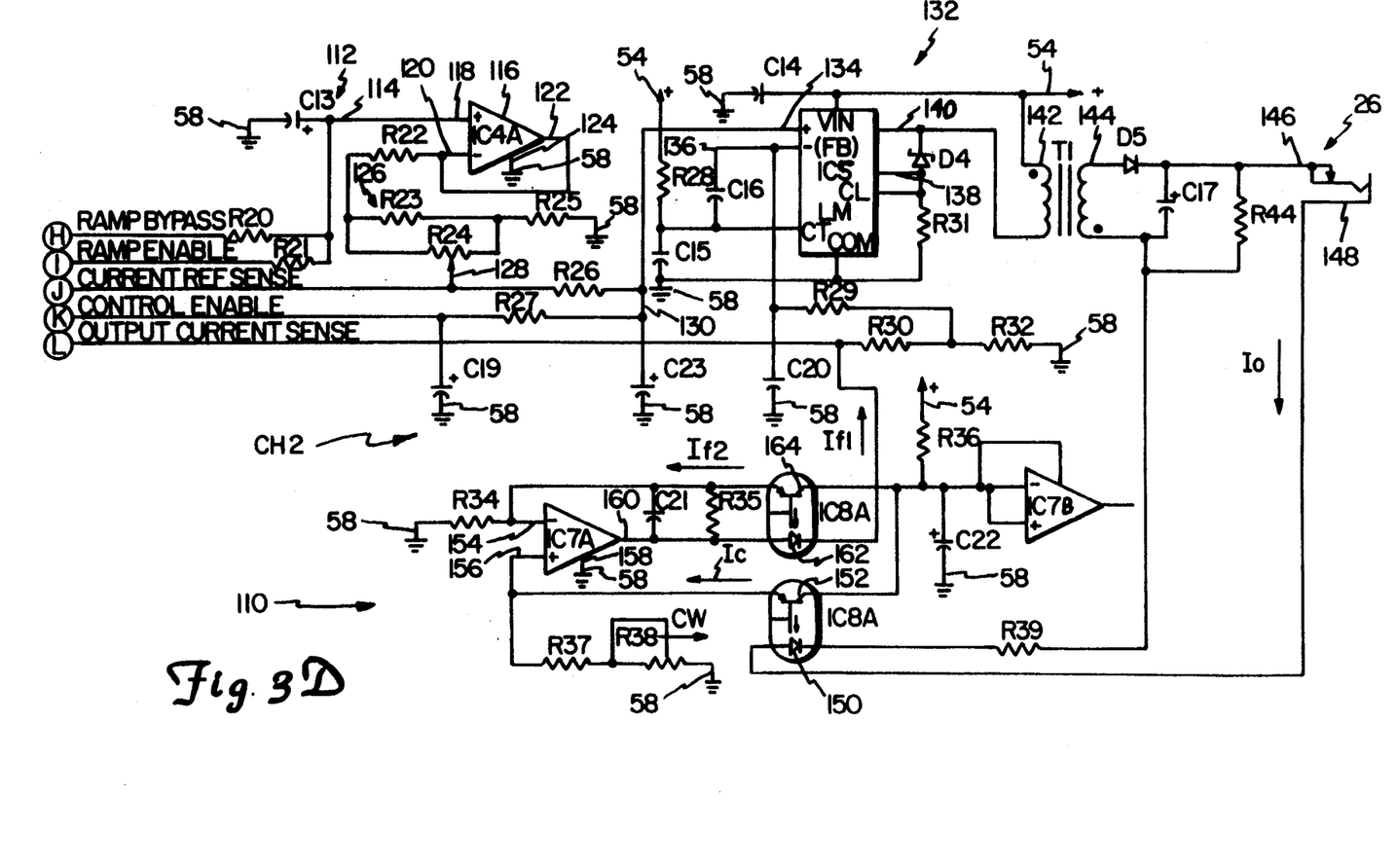
Figure 3E:
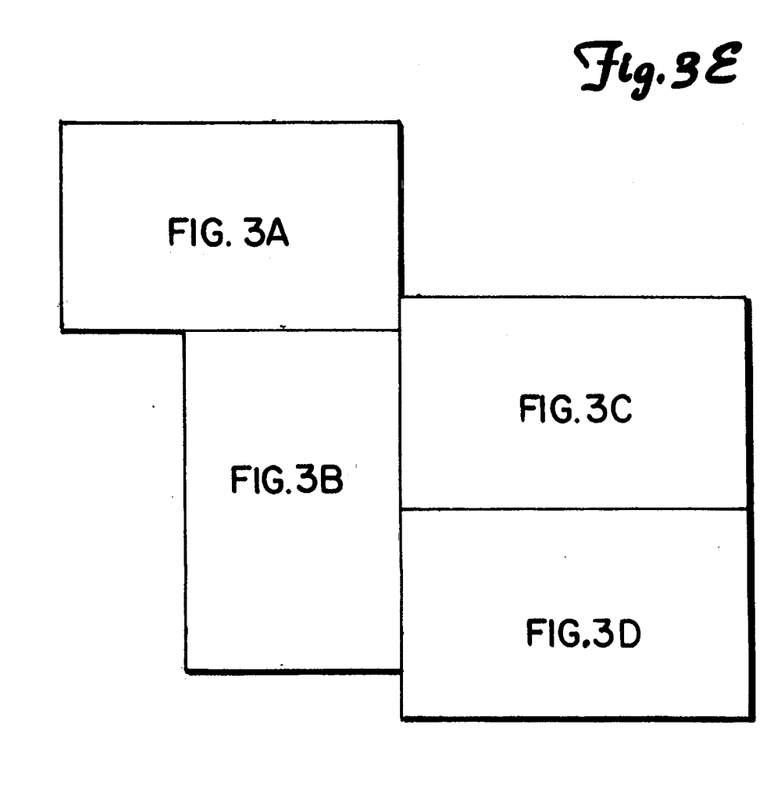

FIGS. 3a, 3b, 3c and 3d together form a detailed schematic diagram of iontophoresis device 10 shown in FIGS. 1-2. FIG. 3e is a block diagram which illustrates how FIGS. 3a, 3b, 3c and 3d are to be arranged. FIG. 3a is arranged above FIG. 3b. FIGS. 3c and 3d are arranged to the right of FIG. 3b, with FIG. 3c above FIG. 3d.

As shown in FIG. 3a, iontophoresis device 10 includes power supply 50. Power supply 50 includes power switch 46, battery 52, diode D1, capacitors C1, C2, C3, C4 and C5, resistors R1, R2 and R3, voltage regulators IC1 and IC2, voltage supply terminals 54 and 56, and ground terminal 58.

Battery 52 is connected between ground terminal 58 and the anode of diode D1. Battery 52 is positioned within battery compartment 48 (shown in FIG. 2). In one embodiment, battery 52 is a 9-volt battery.

Capacitors C1, C2 and C3 are connected together in parallel between the cathode of diode D1 and ground terminal 58. Power switch 46 is connected between the cathode of diode D1 and voltage supply terminal 54. When the user moves power switch 46 to an ON position, battery 52 provides approximately nine volts to voltage supply terminal 54.

Resistor R1 is connected between voltage supply terminal 54 and node 60. Voltage regulator IC2 is connected between node 60 and ground terminal 58. In one embodiment, voltage regulator IC2 provides a regulated 2.5 volt reference voltage on node 60. Resistor R2 is connected between voltage supply terminal 54 and node 62. Resistor R3 is connected between node 62 and ground terminal 58. Capacitor C5 is connected between node 62 and ground terminal 58. Resistors R2 and R3 form a voltage divider and have resistances selected to provide a 2.5 volt battery reference level on node 62. Microprocessor IC3 (shown in FIG. 3b) performs a low battery test to determine when the voltage on voltage supply terminal 54 drops below a selected level. Microprocessor IC3 monitors the battery voltage applied to voltage supply terminal 54 by comparing the regulated 2.5 volt reference voltage on node 60 with the 2.5 volt battery reference voltage on node 62.

Voltage regulator IC1 is connected between voltage supply terminal 54 and ground terminal 58. Voltage regulator IC1 provides a regulated output voltage on voltage supply terminal 56. In one embodiment, voltage regulator IC1 provides a regulated 5 volt output voltage on voltage supply terminal 56. Capacitor C4 is connected between voltage supply terminal 56 and ground terminal 58.

As shown in FIG. 3b, iontophoresis device 10 includes microprocessor IC3. Microprocessor IC3 can include any suitable, commercially available microprocessor. In one embodiment, microprocessor IC3 is a uPD75P328PG microprocessor that is programmed with firmware to provide means for acquiring data, making calculations, and effecting appropriate operations of the device.

Microprocessor IC3 includes numerous input and output terminals. Voltage input terminal VDD is connected to voltage supply terminal 56 to provide power to microprocessor IC3. Voltage reference terminal AVref is connected to node 60 (shown in FIG. 3a) to monitor the regulated reference voltage. Terminal AN0 is connected to node 62 to monitor the battery reference voltage.

Microprocessor terminal P20 is connected to the gate of transistor Q1. Buzzer 64 is connected between the drain of transistor Q1 and voltage supply terminal 54. The source of transistor Q1 is connected to ground terminal 58. Buzzer 64 provides audible status or warning signals to the user.

Iontophoresis device 10 includes light emitting diodes (LEDs) DS1 and DS2 which illuminate when the device delivers current to output jacks 24 and 26, respectively. LEDs DS1 and DS2 correspond to LEDs 28 and 30 shown in FIGS. 1 and 2. Resistor R18 is connected between the cathode of LED DS1 and microprocessor terminal P40. The anode of LED DS1 is connected to voltage supply terminal 56. Resistor R19 is connected between the cathode of LED DS2 and microprocessor terminal P41. The anode of LED DS2 is connected to voltage supply terminal 56. Microprocessor IC3 provides a logic LOW signal on terminals P40 and P41 when current is being delivered to channel 1 electrode output jack 24 and channel 2 electrode output jack 26, respectively.

Dose increment switch 40 is connected between microprocessor terminal P70 and ground terminal 58. Dose decrement switch 42 is connected between microprocessor terminal P71 and ground terminal 58. Dose increment and dose decrement switches 40 and 42 are momentary contact push button switches that increment and decrement the selected drug dose. Display selector switch 44 is connected between microprocessor terminal P60 and ground terminal 58. Display selector switch 44 is a momentary contact push button switch which determines whether time, dose, or current is displayed on LCD display 16. Treatment control switch 18 is connected between microprocessor terminal P10, microprocessor terminal P11 and ground terminal 58. Treatment control switch 18 selects between setup channel 1, setup channel 2, pause, and run modes of microprocessor IC3.

Microprocessor IC3 is driven by a crystal resonator circuit CR1 which is connected between voltage supply terminal 56 and microprocessor terminals X1 and X2. Crystal resonator circuit CR1 provides the primary timing for microprocessor IC3.

Iontophoresis device 10 includes a reset circuit formed by resistor R33, diode D6, and capacitor C18. Resistor R33 is connected between voltage supply terminal 56 and active-low microprocessor reset terminal (RESET). The anode of diode D6 is connected to microprocessor reset terminal (RESET). The cathode of diode D6 is connected to voltage supply terminal 56. Capacitor C18 is connected between microprocessor reset terminal (RESET) and ground terminal 58. The reset circuitry provides an initial logic LOW signal to the active-low microprocessor reset terminal (RESET) when iontophoresis device 10 is turned on to reset microprocessor IC3.

Microprocessor IC3 further includes unused terminals VSS, P00, P01, P02, P03, P12, P13, AN3, AVSS, XT1, P61, P62, P63, P72, and P73. These terminals are all connected to ground terminal 58.

Resistors R40, R41, and R42 establish voltage bias levels for microprocessor terminals BIAS, VIc0, VIc1, and VIc2. Resistor R40 is connected between terminal VIc1 and terminals BIAS and VIc0. Resistor R41 is connected between terminals VIc1 and VIc2. Resistor R42 is connected between terminal VIc2 and ground terminal 58.

Liquid crystal display (LCD) 16 is connected to microprocessor IC3 through microprocessor terminals S12, S13, S14, S15, S16, S17, S18, S19, S20, S21, S22, S23, S24, S25, S26, COM0, COM1, COM2, COM3. LCD display 16 selectively displays treatment parameters for channel 1 and channel 2 including dose delivered, time remaining, and current level.

Microprocessor IC3 includes a set of output terminals for controlling each electrode driver channel. Terminals P30, P80, AN4, P50, and AN1 control operation of electrode driver channel 1, labeled as "CHi"(shown in FIG. 3c). Terminals P31, P81, AN5, P51, and AN2 control operation of electrode driver channel 2, labeled as "CH2"(shown in FIG. 3d).

With respect to electrode driver channel CH1, microprocessor IC3 provides a ramp voltage (logic HIGH, 5 volts) on ramp bypass terminal P30 and an open circuit on ramp enable terminal P80 during pause mode to bypass the output current ramp. This enables the user to select the desired current intensity by adjusting channel 1 current intensity knob 20 (shown in FIG. 1) without having to wait for the current to ramp up and ramp down. Microprocessor IC3 monitors the current to be delivered through electrode output jack 24 by monitoring the voltage on current reference sense terminal AN4. Microprocessor IC3 displays the selected current intensity to be delivered on LCD display 16.

Control enable terminal P50 enables and disables electrode driver channel CH1. During setup mode and pause mode, microprocessor IC3 provides a logic LOW signal on control enable terminal P50 to prevent electrode driver channel CH1 from delivering current through electrode output jack 24. When electrode driver channel CH1 is disabled, the user can select the desired dosage and current intensity without delivering current to the electrodes connected to electrode output jack 24.

When the patient moves treatment control switch 18 from pause mode to run mode, microprocessor IC3 provides an open circuit on ramp bypass terminal P30, the ramp voltage on ramp enable terminal P80, and an open circuit on control enable terminal P50. Control enable terminal P50 enables electrode driver channel CH1 to deliver current through electrode output jack 24. The current ramps up exponentially from zero to the selected current intensity and remains at the selected current intensity until the prescribed dose (in milliampere-minutes) is delivered to the patient. Microprocessor IC3 monitors the total current delivered to the patient by monitoring the voltage on output current sense terminal AN1.

At the end of the treatment period, microprocessor IC3 removes the ramp voltage from ramp enable terminal P80 so that the current delivered through electrode output jack 24 ramps down to zero to complete the treatment. The operation of electrode driver channel CH2 through microprocessor terminals P31, P81, AN5, P51 and AN2 is substantially similar to the operation of electrode driver channel CH1.

CHANNEL ONE

FIG. 3c is a schematic diagram of electrode driver channel CH1. Electrode driver channel CH1 is connected to microprocessor IC3 (shown in FIG. 3b) through ramp bypass terminal P30, ramp enable terminal P80, current reference sense terminal AN0, control enable terminal P50, and output current sense terminal AN1.

Electrode driver channel CH1 includes an RC circuit 69 formed by resistors R4 and R5 and capacitor C6. Resistor R4 is connected between ramp bypass terminal P30 and capacitor C6. Resistor R5 is connected between ramp enable terminal P80 and capacitor C6. Capacitor C6 is connected between ground terminal 58 and resistors R4 and R5. RC circuit 69 includes an RC output 70 which generates an RC output voltage in response to the ramp voltage selectively applied to ramp bypass terminal P30 and ramp enable terminal P80.

RC circuit 69 has a time constant which is selectable in magnitude between a first time constant and a second time constant. Resistor R4 has a substantially smaller resistance than resistor R5. When microprocessor IC3 applies the ramp voltage to ramp bypass terminal P30, as opposed to ramp enable terminal P80, capacitor C6 charges very quickly through resistor R4 with a relatively small time constant. The RC output voltage at RC output 70 rises exponentially from zero to five volts in a few milliseconds.

When microprocessor IC3 applies the ramp voltage to ramp enable terminal P80, capacitor C6 charges very slowly through resistor R5 with a relatively large time constant. The RC output voltage at RC output 70 rises exponentially from zero to five volts in approximately 10–60 seconds.

Electrode driver channel CH1 includes a voltage follower 71 which is connected to RC output 70. Voltage follower 71 includes an amplifier IC4B having a non-inverting input 72, an inverting input 74, a supply terminal 76, and an output terminal 78. Non-inverting input 72 is connected to RC output 70. Voltage supply terminal 76 is connected to voltage supply terminal 58. Output terminal 70 is connected to inverting input 74. The voltage on output terminal 78 follows the RC output voltage on RC output 70.

Electrode driver channel CH1 includes an adjustable voltage divider 79 formed by resistors R6, R7, R8, and R9. Resistor R6 is connected between non-inverting amplifier input 74 and resistor R7. Resistor R7 is connected in parallel with variable resistor R8. Resistor R9 is connected between resistor R7 and ground terminal 58. Variable resistor R8 includes a wiper 80 which is controlled by current intensity knob 20 (shown in FIG. 1). Wiper 80 is connected to resistor R10 and to current reference sense terminal AN4 of microprocessor IC3. Resistor R10 is connected between wiper 80 and node 82. The voltage generated by adjustable voltage divider 79 on wiper 80 represents the current intensity to be delivered by electrode driver channel CH1 through electrode output jack 24. This voltage forms a modulation treatment control voltage which is applied to switching regulator IC6.

Microprocessor IC3 monitors the modulation treatment control voltage during pause mode and determines the current intensity to be delivered through electrode output jack 24. Microprocessor IC3 displays the current to be delivered on LCD display 16.

Resistor R11 is connected between node 82 and control enable terminal P50. Capacitor C12 is connected between control enable terminal P50 and ground terminal 58. Microprocessor IC3 prevents electrode driver channel CH1 from delivering current through electrode output jack 24 during pause mode by providing a logic LOW signal on control enable terminal P50. The LOW signal pulls node 82 LOW to prevent the modulation treatment control voltage on wiper 80 from reaching switching regulator IC6. When microprocessor IC3 provides an open circuit on control enable terminal P50, resistor R11 is essentially removed from the circuit so that the modulation treatment control voltage on wiper 80 can reach switching regulator IC6, causing current to be delivered through electrode output jack 24.

Electrode driver channel CH1 further includes a "flyback" regulator circuit 84 for regulating the electrode output current delivered through electrode output jack 24. Flyback regulator circuit 84 includes switching regulator IC6, transformer T2, resistors R12, R13, R14, R15, R16, R17 and R43, capacitors C7, C8, C9 and C10, and diodes D2 and D3. Switching regulator IC6 is connected to operate as a pulse width modulator to generate a pulse width modulated signal for transformer T2.

Switching regulator IC6 includes a voltage input terminal VIN, a voltage common terminal COM, a modulation control terminal 86, a modulation feedback terminal 88, a capacitor timing terminal CT, a collector terminal 90, an emitter terminal 92, and a current limit terminal CL. Modulation control terminal 86 is connected to node 82. Capacitor C8 is connected between modulation feedback terminal 88 and capacitor timing terminal CT. Resistor R12 is connected between voltage supply terminal 54 and capacitor timing terminal CT. Capacitor C7 is connected between capacitor timing terminal CT and ground terminal 58. Voltage common terminal COM is connected to ground terminal 58. Resistor R13 is connected between current limit terminal CL and voltage common terminal COM. Current limit terminal CL is connected to emitter terminal 92. Emitter terminal 92 is connected to the anode of diode D2. The cathode of diode D2 is connected to collector terminal 90. Capacitor C9 is connected between voltage input terminal VIN and ground terminal 58.

Transformer T2 includes a primary winding 94 and a secondary winding 96. Primary winding 94 is connected between voltage supply terminal 54 and collector terminal 90. Secondary winding 96 is connected between the anode of diode D3 and ground terminal 58. Capacitor C10 is connected between the cathode of diode D3 and ground terminal 58. Diode D3 and capacitor C10 form a rectifier which rectifies current induced in secondary winding 96.

Electrode output jack 24 includes terminals 98 and 100. Resistor R43 is connected between terminal 98 and ground terminal 58. Resistor R15 is connected between terminal 100 and node 102. Resistor R16 is connected between node 102 and node 104. Resistor R17 is connected between node 104 and ground terminal 58. Resistor R14 is connected between node 104 and modulation feedback terminal 88 of switching regulator IC6.

Resistors R15, R16 and R17 are connected in series to form a voltage divider. Node 102 is connected to microprocessor output current sense terminal AN1 (shown in FIG. 3b) to provide microprocessor IC3 with a feedback voltage representative of the electrode output current delivered through electrode output jack 24.

As mentioned above, switching regulator IC6 is connected to operate as a pulse width modulator. Switching regulator IC6 includes a comparator (not shown) having inputs connected to modulation control terminal 86 and modulation feedback terminal 88. Switching regulator IC6 includes an output transistor (also not shown) having a collector connected to collector terminal 90 and an emitter connected to emitter terminal 92. Switching regulator IC6 generates a pulse width modulated output signal through collector terminal 90 and emitter terminal 92 as a function of the modulation treatment control voltage applied to modulation control terminal 86 and the modulation feedback voltage applied to modulation feedback terminal 88.

The modulation treatment control voltage and the modulation feedback voltage control the pulse width of the modulated output signal. As the modulation treatment control voltage increases, the pulse width of the modulated output signal increases. As the modulation treatment control voltage decreases, the pulse width of the modulated output signal decreases. Capacitor C7 has a capacitance which is selected to establish a desired switching frequency of the modulated output signal. Resistor R12 has a resistance which is selected to limit the pulse width of the modulated output signal. Resistor R13 has a resistance which is selected to limit the magnitude of current generated through primary winding 94 and through the output transistor of switching regulator IC6.

When the output transistor of switching regulator IC6 is ON, current flows through collector terminal 90 and emitter terminal 92. The current increases linearly within primary winding 94 and secondary winding 96, which charges capacitor C10.

Unlike a normal transformer, transformer T2 operates as an inductor which stores substantial energy in its flux. When the output transistor of switching regulator IC6 turns OFF, the flux in transformer T2 begins to decrease causing current to flow in secondary winding 96. The current in secondary winding 96 maintains the voltage across capacitor C10 substantially constant. The voltage across capacitor C10 maintains a substantially constant electrode output current through electrode output jack 24.

If the pulse width of the modulated output signal increases, the current flowing through primary winding 94 increases which increases the energy stored in the flux of transformer T2. The increased flux energy causes the current flowing through secondary winding 96 to increase when the output transistor of switching regulator of IC6 is OFF. Therefore, an increase in pulse width causes an increase in current intensity in the electrode output current. Similarly, a decrease in the pulse width causes a decrease in the current intensity of the electrode output current.

The modulation feedback voltage applied to modulation feedback terminal 88 provides a closed loop control of the pulse width modulator to maintain the electrode output current at a constant value.

OPERATION OF CHANNEL ONE

In operation, the user first selects a prescribed dose by moving treatment control switch 18 (shown in FIG. 3b and FIG. 1) to select setup mode for channel 1. To display the selected dose on LCD display 16, the user presses display selector switch 44. The user then presses dose increment switch 40 and dose decrement switch 42 select the prescribed treatment dose in milliampere-minutes while monitoring the selected dose on LCD display 16.

During setup mode, microprocessor IC3 provides a logic LOW signal on control enable terminal P50 to disable switching regulator IC6 by forcing the pulse width of the modulated output signal to zero. With a zero pulse width, the modulated output signal from switching regulator IC6 generates no electrode output current through electrode output jack 24.

Next, the user moves treatment control switch 18 from setup mode to pause mode and adjusts the electrode output current to a selected intensity. Microprocessor IC3 maintains the logic LOW signal on control enable terminal P50. Microprocessor IC3 provides the ramp voltage on ramp bypass terminal P30 and a logic LOW signal on ramp enable terminal P80 to disable the ramping feature. Capacitor C6 quickly charges through resistor R4 to the ramp voltage (5 volts) provided on ramp bypass terminal P30.

Voltage follower 71 provides the RC output voltage to adjustable voltage divider 79. Adjustable voltage divider 79 generates the modulation treatment control voltage on wiper 80. Microprocessor IC3 monitors the modulation treatment control voltage and determines the current intensity to be delivered to electrode output jack 24 based upon the magnitude of the modulation treatment control voltage. The current intensity can be displayed on LCD display 16 by pressing display selector switch 44. The user adjusts channel 1 current intensity knob 20 to adjust wiper 80 and thereby select the current intensity to be delivered to electrode output jack 24 while watching the selected current intensity on LCD display 16.

To begin the treatment, the user moves treatment control switch 18 from pause mode to run mode. Microprocessor IC3 first discharges capacitor C6 through resistor R4 by providing a logic LOW signal on ramp bypass terminal P30. After capacitor C6 has discharged, microprocessor IC3 provides an open circuit on control enable terminal P50 to enable switching regulator IC6. Microprocessor IC3 provides the ramp voltage on ramp enable terminal P80. The RC output voltage on RC output 70 increases exponentially from zero to five volts over a period of about 10–60 seconds in response to the ramp voltage. In one preferred embodiment, the RC output voltage increases exponentially from zero to five volts over a period of about 30 seconds.

The voltage on voltage follower output 78 increases exponentially as it follows the RC output voltage. Adjustable voltage divider 79 divides the RC output voltage into the selected modulation treatment control voltage. As the modulation treatment control voltage on modulation control input 86 increases exponentially with the RC output voltage, the pulse width of the modulated output signal of switching regulator IC6 increases exponentially, thereby causing the electrode output current delivered through electrode output jack 24 to increase exponentially to the selected current intensity.

Microprocessor IC3 monitors the electrode output current delivered through electrode output jack 24 by monitoring the feedback voltage applied to output current sense terminal AN1. Microprocessor IC3 determines the total dose delivered to the patient in milliampere-minutes as a function of elapsed time and the feedback voltage on output current sense terminal AN1. The patient can monitor the dose delivered by pressing display selector switch 44 to display the dose delivered on LCD display 16.

After the selected dose is delivered, microprocessor IC3 provides a logic LOW signal on ramp enable terminal P80. Capacitor C6 discharges exponentially through resistor R5 causing the RC output voltage on RC output 70 to decrease exponentially. As a result, the modulation treatment control voltage on modulation control input 86 decreases exponentially causing the pulse width of the modulated output signal of switching regulator IC6 to decrease exponentially. As the pulse width decreases exponentially, the electrode output current decreases exponentially from the selected current intensity to zero. After the electrode output current has decreased to zero, microprocessor IC3 disables switching regulator IC6 by providing a logic LOW signal on control enable terminal P50 to complete the treatment cycle.

CHANNEL TWO

FIG. 3d is a schematic diagram of electrode driver channel CH2. Electrode driver channel CH2 is substantially similar to electrode driver channel CH1. However, electrode driver channel CH2 includes an optically isolated feedback circuit 110 connected between electrode output jack 26 and microprocessor IC3.

Electrode driver channel CH2 includes an RC circuit 112 formed by capacitor C13 and resistors R20 and R21. RC circuit 112 includes an RC output 114. Capacitor C13 is connected between RC output 114 and ground terminal 58. Resistor R20 is connected between RC output 114 and ramp bypass terminal P31 of microprocessor IC3 (shown in FIG. 3b). Resistor R21 is connected between RC output 114 and ramp enable terminal P81.

Electrode driver channel CH2 includes a voltage follower 116 formed by amplifier IC4A. Amplifier IC4A includes a non-inverting input 118, an inverting input 120, an output 122 and a ground terminal 124. Non-inverting input 118 is connected to RC output 114. Amplifier output 122 is connected to inverting input 120. Ground terminal 124 is connected to ground terminal 58.

Electrode driver channel CH2 includes a voltage divider 126 formed by resistors R22, R23, R24, and R25. Resistor R22 is connected between amplifier inverting input 120 and resistor R23. Resistor R23 is connected between resistor R22 and R25. Resistor R25 is connected between resistor R23 and ground terminal 58. Resistor R24 is connected in parallel across resistor R23. Resistor R24 is a variable resistor having a wiper 128 for adjusting the voltage division through voltage divider 126. Wiper 128 is connected to channel 2 current intensity knob 22 (shown in FIG. 1). The user adjusts the voltage division by adjusting channel 2 current intensity knob 22. Wiper 128 is connected to current reference sense terminal AN5 of microprocessor IC3 (shown in FIG. 3b). Resistor R26 is connected between wiper 128 and a node 130.

Electrode driver channel CH2 includes resistor R27 and capacitors C19 and C23 for enabling and disabling the voltage at node 130. Resistor R27 is connected between node 130 and control enable terminal P51. Capacitor C19 is connected between control enable terminal P51 and ground terminal 58. Capacitor C23 is connected between node 130 and ground terminal 58.

Electrode driver channel CH2 further includes a flyback regulator circuit 132. Flyback regulator circuit 132 includes switching regulator IC5, transformer T1, resistors R28, R29, R30, R31, R32 and R44, capacitors C14, C15, C16, C17 and C20, and diodes D4 and D5.

Switching regulator IC5 is connected to operate as a pulse width modulator. Switching regulator IC5 includes a voltage input terminal VIN, a modulation control terminal 134, a modulation feedback terminal 136, a capacitor timing terminal CT, a voltage common terminal COM, a current limit terminal CL, an emitter terminal 138, and a collector terminal 140. Modulation control terminal 134 is connected to node 130. Capacitor C16 is connected between modulation feedback terminal 136 and capacitor timing terminal CT. Resistor R28 is connected between voltage supply terminal 54 and capacitor timing terminal CT. Capacitor C15 is connected between capacitor timing terminal CT and ground terminal 58. Capacitor C20 is connected between modulation feedback terminal 136 and ground terminal 58. Voltage common terminal COM is connected to ground terminal 58. Resistor R31 is connected between current limit terminal CL and voltage common terminal COM. Current limit terminal CL is connected to emitter terminal 138 and to the anode of diode D4. The cathode of diode D4 is connected to collector terminal 140. Resistor R29 and resistor R32 are connected together in series between modulation feedback terminal 136 and ground terminal 158. Resistor R30 is connected between resistor R32 and output current sense terminal AN2 of microprocessor IC3 (shown in FIG. 3b).

Transformer T1 includes a primary winding 142 and a secondary winding 144. Primary winding 142 is connected between voltage supply terminal 154 and collector terminal 140 of switching regulator IC5. Diode D5 and capacitor C17 are connected in series across secondary winding 144, with the anode of diode D5 connected to secondary winding 144 and the cathode of diode D5 connected to capacitor C17. Resistor R44 is connected in parallel across capacitor C17. Electrode output jack 26 includes terminals 146 and 148. Terminal 146 is connected to the cathode of diode D5. Terminal 148 is connected to optically isolated feedback circuit 110.

Electrode driver channel CH2 operates substantially similar to electrode driver channel CH1. Microprocessor IC3 provides a ramp voltage on either ramp bypass terminal P31 or ramp enable terminal P81 to charge capacitor C13 and provide an RC output voltage on RC output 114. Voltage follower 116 generates a voltage on output 122 which follows the RC output voltage. Voltage divider 126 divides the RC output voltage into a modulation treatment control voltage on wiper 128 of variable resistor R24. The modulation treatment control voltage is applied to modulation control terminal 134 of switching regulator 125 to generate a pulse width modulated output signal through collector terminal 140 and emitter terminal 138. Transformer T1 receives the pulse width modulated output signal and delivers an electrode output current (Io) through electrode output jack 26. Diode D5 and capacitor C17 rectify electrode output current Io.

As mentioned above, electrode driver channel CH2 includes optically isolated feedback circuit 110, which is connected between electrode output jack 26 and output current sense terminal AN2 of microprocessor IC3. Optically isolated feedback circuit 110 senses current Io and generates a mirrored, isolated feedback current If1. Feedback current If1 generates a feedback voltage through resistors R30 and R32 which is monitored by microprocessor IC3 on output current sense terminal AN2. The feedback voltage is representative of the current intensity delivered through electrode output jack 26.

Isolated feedback circuit 110 includes amplifier IC7A, optical isolators IC8A and IC8B, resistors R34, R35, R36, R37, R38 and R39, and capacitors C21 and C22. Amplifier IC7B is an unused amplifier within an integrated circuit comprising amplifier IC7A. Optical isolator IC8B includes a light emitting diode (LED) 150 and a phototransistor 152. The anode of LED 150 is connected to electrode output terminal 148. Resistor R39 is connected in series between the cathode of LED 150 and secondary winding 144 of transformer T1. The collector of phototransistor 152 is connected to capacitor C22 and resistor R36. Capacitor C22 is connected between resistor R36 and ground terminal 58. Resistor R36 is connected between capacitor C22 and voltage supply terminal 54. The emitter of phototransistor 152 is connected to resistor R37. Resistor R37 and R38 are connected in series between the emitter of phototransistor 152 and ground terminal 58. Resistor R38 is a variable resistor.

Amplifier IC7A includes an inverting input 154, a non-inverting input 156, a ground terminal 158, and an output 160. Ground terminal 158 is connected to ground terminal 58. Non-inverting input 156 is connected to the emitter of phototransistor 152 and resistor R37. Resistor R34 is connected between inverting amplifier input 154 and ground terminal 58. Capacitor C21 is connected between amplifier output 160 and inverting amplifier input 154. Resistor R35 is connected in parallel with capacitor C21.

Optical isolator IC8A includes a light emitting diode (LED) 162 and a phototransistor 164. The anode of LED 162 is connected to amplifier output 160. The cathode of LED 162 is connected to resistor R30 and to output current sense terminal N2 of microprocessor IC3. The collector of phototransistor 164 is connected to resistor R36, the collector of phototransistor 152 and capacitor C22. The emitter of phototransistor 164 is connected to inverting amplifier input 154.

When electrode driver channel CH2 delivers electrode output current Io through electrode output jack 26, LED 150 generates infrared signals which energize phototransistor 152. Phototransistor 152 generates a control current Ic which is representative of electrode output current Io. Resistors R37 and R38 convert control current Ic into a control voltage which is applied to non-inverting amplifier input 156.

Amplifier IC7A generates feedback current If1 on amplifier output 160 as a function of the control voltage applied to non-inverting amplifier input 156 and a feedback voltage applied to inverting amplifier input 154. Feedback current If1 flows through LED 162 which generates infrared signals that energize phototransistor 164. Phototransistor 164 generates feedback current If2 which is representative of feedback current If1. Resistor R34 converts feedback current If2 into the feedback voltage that is applied to inverting amplifier input 154.

Amplifier IC7A controls the level of feedback current If1 through output 160 to maintain the voltages at amplifier input terminals 154 and 156 substantially equal. If the transfer ratios of optical isolators IC8A and IC8B are equal and resistor R34 has a resistance that is equal to the combined resistance of resistors R37 and R38, then feedback current If1 will be substantially equal to electrode output current Io. Resistors R30 and R32 convert feedback current If1 into the feedback voltage that is monitored by microprocessor IC3 on output current sense terminal AN2.

Optically isolated feedback circuit 110 is discussed in greater detail in copending U.S. application Ser. No. 07/851,052, filed Mar. 13, 1992, for an ISOLATED CURRENT MIRROR WITH OPTICAL ISOLATOR GENERATING FEEDBACK SIGNAL and in copending U.S. Application, filed Nov. 16, 1992, for a LOW POWER, OPTICALLY ISOLATED CURRENT MIRROR HAVING FEEDBACK WITH OPTICAL ISOLATION. The copending applications are hereby incorporated by reference.

Transformers T1 and T2 and optically isolated feedback circuit 110 provide complete isolation between channel 1 electrode output jack 24 and channel 2 electrode output jack 26 to allow accurate, independent and controlled dose delivery through each electrode driver channel.

The circuit components and values of the elements shown in FIGS. 3a, 3b, 3c and 3d are shown below in table 1. The specific components and values shown in table 1 are provided only as an example and can be replaced with other components or values without departing from the spirit and scope of the invention.

TABLE 1

| ELEMENT | COMPONENT/VALUE |
|---|---|
| IC1 | LP2950 |
| IC2 | LM385 |
| IC3 | uPD75P328PG |
| IC4A, IC4B | LM358 |
| IC5 | LM3578AN |
| IC6 | LM3578AN |
| IC7A, IC7B | LM358 |
| IC8A, IC8B | PC827 |
| Q1 | ZVN2106 |
| D1 | BYV10-20 |
| D2 | 1N5256 |
| D3 | BAV21 |
| D4 | 1N5256 |
| D5 | BAV21 |
| D6 | BAV21 |
| C1 | 470 µF, 10 V |
| C2 | 470 µF, 10 V |
| C3 | 10 µF, 16 V |
| C4 | 1 µF, 35 V |
| C5 | 1 µF, 35 V |
| C6 | 10 µF, 16 V |
| C7 | 0.001 µF |
| C8 | 22 pF |
| C9 | 0.1 µF |
| C10 | 2.2 µF, 100 V |
| C12 | 10 µF, 16 V |
| C13 | 10 µF, 16 V |
| C14 | 0.1 µF |
| C15 | 0.001 µF |
| C16 | 22 pF |
| C17 | 2.2 µF |
| C18 | 0.33 µF, 50 V |
| C19 | 10 µF, 10 V |
| C20 | 0.1 µF |
| C21 | 0.1 µF |
| C22 | 10 µF, 10 V |
| C23 | 0.1 µF |
| R1 | 1.1k ohm |
| R2 | 150k ohm |
| R3 | 49.9k ohm |
| R4 | 100 ohm |
| R5 | 1M ohm |
| R6 | 5.49k ohm |
| R7 | 1.1k ohm |
| R8 | 10k ohm |
| R9 | 432 ohm |
| R10 | 10k ohm |
| R11 | 5.11k ohm |
| R12 | 100k ohm |
| R13 | 1 ohm |
| R14 | 10k ohm |
| R15 | 499 ohm |
| R16 | 249 ohm |
| R17 | 249 ohm |
| R18 | 47.5 ohm |
| R19 | 47.5 ohm |
| R20 | 100 ohm |
| R21 | 1M ohm |
| R22 | 5.49k ohm |
| R23 | 1.1k ohm |
| R24 | 10k ohm |
| R25 | 432 ohm |
| R26 | 10k ohm |
| R27 | 5.11k ohm |
| R28 | 100 ohm |
| R29 | 10k ohm |
| R30 | 249 ohm |
| R31 | 1 ohm |
| R32 | 249 ohm |
| R33 | 100k ohm |
| R34 | 475 ohm |
| R35 | 200k ohm |
| R36 | 47.5 ohm |
| R37 | 374 ohm |
| R38 | 200 ohm |
| R39 | 1k ohm |
| R40 | 100k ohm |
| R41 | 100k ohm |
| R42 | 100k ohm |
| R43 | 1M ohm |
| R44 | 1M ohm |

CONCLUSION

The multiple site drug iontophoresis electronic device of the present invention is capable of delivering ionic drugs through two pair of iontophoresis electrodes independently. The device includes two electrode driver channels, with each driver channel having an electrode output that is electrically isolated and independently controlled in current intensity. The user can place the iontophoresis electrode pairs on the same site or on different sites to customize the treatment for each application.

Since the electrode output of one channel is electrically isolated from the electrode output of the other channel, the microprocessor can accurately control the dosage delivered by each channel. In bifurcated, single channel devices, current division between electrodes is uncontrollable.

The microprocessor allows the user to simply select a target dosage and start drug delivery. The electrode output current automatically ramps up exponentially from zero to a selected current intensity at the beginning of a treatment period and automatically ramps down exponentially to zero at the end of the treatment period for patient comfort and safety. The exponential rise and fall of the electrode output current maximizes patient comfort while minimizing treatment time. If the electrode output current intensity requires adjustment, the microprocessor automatically recalculates the treatment parameters to insure delivery of the proper dosage.

Although the present invention has been described with reference to preferred embodiments, workers skilled in the art will recognize that changes may be made in form and detail without departing from the spirit and scope of the invention. For example, workers skilled in the art will recognize that the particular components selected for the embodiment shown in FIGS. 3a, 3b, 3c and 3d can be replaced with various other components and that the particular circuit configuration shown can be changed without departing from the spirit and scope of the invention.

What is claimed is:

1. An iontophoresis controller which adjusts current to an iontophoresis electrode pair to control infusion of a selected dose of ionic drugs into a patient through the electrode pair during a treatment period, the controller comprising:

an electrode driver channel generating an electrode output current which has an intensity that rises exponentially from approximately zero to a selected treatment current intensity, remains at the selected treatment current intensity, and then falls exponentially to approximately zero, the electrode driver channel having an electrode output adapted to be connected to the electrode pair to deliver the electrode output current to the electrode pair; and means for controlling the electrode driver channel to generate the electrode output current during the treatment period, thereby controlling infusion of the selected dose of ionic drugs into the patient through the electrode pair during the treatment period.

2. The iontophoresis controller of claim 1 wherein:

the means for controlling the electrode driver channel comprises a microprocessor which selectively applies a ramp voltage to a ramp enable output; and the electrode driver channel further comprises:

an RC circuit having a resistance and a capacitance connected in series with the ramp enable output such that the RC circuit generates an RC output voltage that rises exponentially from approximately zero to the ramp voltage when the microprocessor applies the ramp voltage to the ramp enable output and falls exponentially from the ramp voltage to approximately zero when the microprocessor removes the ramp voltage from the ramp enable output; and means connected to the RC circuit for delivering the electrode output current through the electrode output as a function of the RC output voltage.

3. The iontophoresis controller of claim 2 wherein the RC circuit has a time constant which is selectable in magnitude between a first time constant and a second time constant and wherein the second time constant is larger than the first time constant.

4. The iontophoresis controller of claim 3 wherein:

the microprocessor further comprises a ramp bypass output which selectively applies the ramp voltage to one of the ramp bypass output and the ramp enable output; and the RC circuit resistance comprises a first resistor which is connected between the ramp bypass output and the capacitance, and a second resistor connected between the ramp enable output and the capacitance, wherein the first resistor has a first resistance such that the RC output voltage rises and falls exponentially with the first time constant when the ramp voltage is applied to the ramp bypass output and wherein the second resistor has a second resistance, larger than the first resistance, such that the RC output voltage rises and falls exponentially with the second time constant when the ramp voltage is applied to the ramp enable output.

5. The iontophoresis controller of claim 2 wherein the means for delivering the electrode output current as a function of the RC output voltage comprises:

an amplifier connected to the RC circuit in a voltage follower configuration which receives the RC output voltage and generates an amplifier output which follows the RC output voltage;

an adjustable voltage divider which has an input connected to the amplifier output and which has an adjustable voltage divider output, wherein the adjustable voltage divider generates a treatment control voltage on the adjustable voltage divider output which has a magnitude that is a function of the RC output voltage and an adjustment of the adjustable voltage divider; and means for controlling the electrode output current as a function of the treatment control voltage.

6. The iontophoresis controller of claim 5 wherein the microprocessor further comprises:

a control enable output connected to the means for controlling the electrode output current such that the microprocessor selectively applies a control signal on the control enable output which enables and disables the means for controlling the electrode output; and a reference current input connected to the adjustable voltage divider output such that the microprocessor monitors the treatment control voltage generated on the voltage divider output when the means for controlling the electrode output current is disabled and determines the electrode output current to be delivered through the electrode output based on the monitored treatment control voltage.

7. The iontophoresis controller of claim 5 wherein:

the electrode driver channel further comprises:

a feedback circuit having a feedback input connected to the electrode output and having a feedback output such that the feedback circuit generates a feedback voltage on the feedback output as a function of the electrode output current delivered through the electrode output; and the microprocessor further comprises:

a control enable output connected to the means for controlling the electrode output current such that the microprocessor selectively a control signal on the control enable output which enables and disables the means for controlling the electrode output current; and a delivered current input connected to the feedback output such that the microprocessor monitors the feedback voltage generated on the feedback output when the means for controlling the electrode output current is enabled and such that the microprocessor determines the electrode output current delivered through the electrode output based on monitored the feedback voltage.

8. The iontophoresis controller of claim 2 wherein the means for delivering the electrode output current as a function of the RC output voltage comprises:

means for generating a modulation treatment control voltage as a function of the RC output voltage;

a pulse width modulator having a modulation control input, a modulation feedback input and a modulated output such that the modulation control input is connected to the means for generating the modulation treatment control voltage and such that the pulse width modulator generates a modulated signal on the modulated output having a pulse width that is a function of the modulation treatment control voltage and a modulation feedback voltage which is applied to the modulation feedback input;

an isolation transformer having a primary coil and a secondary coil, with the primary coil connected to the modulated output and the secondary coil connected to the electrode output for generating such that the isolation transformer generates the electrode output current in response to the modulated signal received at the primary coil;

a rectifier connected to the secondary coil, which rectifies the electrode output current; and a modulation feedback circuit having an input connected to the electrode output and having an output connected to the modulation feedback input of the pulse width modulator such that the modulation feedback circuit generates the modulation feedback voltage on the modulation feedback circuit output as a function of the electrode output current.

9. The iontophoresis controller of claim 1 wherein the electrode driver channel further comprises:

means for generating a modulation treatment control voltage which rises exponentially from approximately zero to a selected modulation treatment control level, remains at the modulation treatment control level during the treatment period, and then fails exponentially to approximately zero;

a pulse width modulator having a modulation control input, a modulation feedback input and a modulated output such that the modulation control input is connected to the means for generating a modulation treatment control voltage and such that the pulse width modulator generates a modulated signal on the modulated output having a pulse width which is a function of the modulation treatment control voltage and a modulation feedback voltage which is applied to the modulation feedback input;

an isolation transformer having a primary coil and a secondary coil, with the primary coil connected to the modulated output and the secondary coil connected to the electrode output for generating the electrode output current in response to the modulated signal received at the primary coil;

a rectifier connected to the secondary coil, which rectifies the electrode output current; and a modulation feedback circuit having an input connected to the electrode output and having an output connected to the modulation feedback input of the pulse width modulator such that the modulation feedback circuit generates the modulation feedback voltage on the modulation feedback circuit output as a function of the electrode output current.

10. An iontophoresis controller which adjusts current to an iontophoresis electrode pair to control infusion of a selected dose of ionic drugs into a patient through the electrode pair during a treatment period, the controller comprising:

a microprocessor having a ramp enable output such that the microprocessor selectively applies a ramp voltage on the ramp enable output;

an RC circuit having an input connected to the ramp enable output and having an RC output, wherein the RC circuit has a time constant which is selectable in magnitude between a first time constant and a second time constant and wherein the second time constant is larger than the first time constant such that the RC circuit generates an RC output voltage on the RC output as a function of the ramp voltage and the selected time constant;

an electrode output adapted to be electrically connected to the electrode pair; and means connected between the RC circuit and the electrode output for generating an electrode output current through the electrode output which has an intensity that rises exponentially from approximately zero to a selected treatment current intensity, remains at the selected treatment current intensity, and then falls exponentially to approximately zero as a function of the RC output voltage, thereby controlling infusion of the selected dose of ionic drugs into the patient through the electrode pair during the treatment period.

11. An iontophoresis controller which adjust current to an iontophoresis electrode pair to control infusion of a selected dose of ionic drugs into a patient through the electrode pair during a treatment period, the controller comprising:

a microprocessor having a ramp enable output such that the microprocessor selectively applies a ramp voltage on the ramp enable output;

an RC circuit having an RC input connected to the ramp enable output and having an RC output such that the RC circuit generates an RC output voltage on the RC output that rises exponentially from approximately zero to the ramp voltage when the microprocessor applies the ramp voltage to the ramp enable output and falls exponentially from the ramp voltage to approximately zero when the microprocessor removes the ramp voltage from the ramp enable output;

an amplifier connected to the RC output in a voltage follower configuration such that the amplifier receives the RC output voltage and generates an amplifier output signal which follows the RC output voltage;

an adjustable voltage divider having an input connected to the amplifier which receives the amplifier output signal and having a voltage divider output, such that the adjustable voltage divider generates a treatment control voltage on the voltage divider output which has a magnitude that is a function of the amplifier output signal and an adjustment of the adjustable voltage divider;

an electrode output adapted to be electrically connected to the electrode pair; and means connected to the adjustable voltage divider and to the electrode output for generating an electrode output current through the electrode output as a function of the magnitude of the treatment control voltage, thereby controlling infusion of the selected dose of ionic drugs into the patient through the electrode pair during the treatment period.

12. An iontophoresis controller which adjust current to an iontophoresis electrode pair to control infusion of a selected dose of ionic drugs into a patient through the electrode pair during a treatment period, the controller comprising:

an electrode output adapted to be electrically connected to the electrode pair;

means for generating a modulation treatment control voltage which rises exponentially from approximately zero to a selected modulation treatment control level, remains at the modulation treatment control level, and then falls exponentially to approximately zero;

pulse width modulator means having a modulation control input, a modulation feedback input and a modulated output, wherein the modulation control input is connected to the means for generating a modulation treatment control voltage for generating a modulated signal on the modulated output having a pulse width which is a function of the modulation treatment control voltage and a modulation feedback voltage which is applied to the modulation feedback input;

isolation transformer means having a primary coil and a secondary coil, with the primary coil connected to the modulated output and the secondary coil connected to the electrode output for generating an electrode output current in response to the modulated signal received at the primary coil;

a rectifier connected to the secondary coil, which rectifies the electrode output current; and modulation feedback means having an input connected to the electrode output and having an output connected to the modulation feedback input of the pulse width modulator means for generating the modulation feedback voltage on the modulation feedback means output as a function of the electrode output current.

* * * * *